United States Patent [19]

Aguadisch et al.

[11] Patent Number: 4,814,184

[45] Date of Patent: Mar. 21, 1989

[54] PHARMACEUTICAL DELIVERY DEVICE HAVING A SILOXANE POLYMER MATRIX

[75] Inventors: Louis M. J. Aguadisch, Valbonne, France; Frank S. Rankin, South Glamorgan, Wales

[73] Assignee: Dow Corning Ltd., Barry, Wales

[21] Appl. No.: 154,755

[22] Filed: Feb. 9, 1988

[30] Foreign Application Priority Data

Feb. 28, 1987 [GB] United Kingdom ............... 8704755

[51] Int. Cl.$^4$ .............................................. A61K 9/14
[52] U.S. Cl. ..................................... 424/486; 424/78; 424/422; 424/424; 424/425; 424/443; 424/445
[58] Field of Search ................. 424/486, 78, 422, 424, 424/425, 443, 445

[56] References Cited

U.S. PATENT DOCUMENTS

| | | | |
|---|---|---|---|
| 3,710,795 | 1/1973 | Higuchi et al. | 428/486 X |
| 3,777,015 | 12/1973 | Zaffaroni | 424/486 X |
| 3,832,458 | 8/1974 | Merrill | 424/424 |
| 3,909,444 | 9/1975 | Anderson et al. | 424/486 X |
| 3,921,636 | 11/1975 | Zaffaroni | 424/486 |
| 3,992,518 | 11/1976 | Chien et al. | 424/486 X |
| 4,053,580 | 10/1977 | Chien et al. | 424/424 X |
| 4,169,069 | 9/1979 | Unger et al. | 424/486 X |
| 4,191,741 | 3/1980 | Hudson et al. | 424/425 |
| 4,230,686 | 10/1980 | Schopflin et al. | 424/486 X |
| 4,690,683 | 9/1987 | Chien et al. | 424/486 X |

FOREIGN PATENT DOCUMENTS 0013949 8/1980 European Pat. Off. ............ 424/425

Primary Examiner—Thurman K. Page
Attorney, Agent, or Firm—Susan M. Cornwall

[57] ABSTRACT

Improved pharmaceutical delivery devices which can deliver hydrophilic or polar pharmaceutically active materials, as well as optionally hydrophobic or non-polar materials, have small particles with on average a diameter below 20 microns of a drug component comprising the hydrophilic or polar pharmaceutically active material, dispersed in a silicone matrix. These devices are produced by using certain organopolysiloxane-polyoxyalkylene copolymers. Preferably an emulsion of the drug component in a silicone containing composition is made before curing the composition to an elastomer.

17 Claims, No Drawings

PHARMACEUTICAL DELIVERY DEVICE HAVING A SILOXANE POLYMER MATRIX

This invention relates to pharmaceutical delivery devices and also to a method for making such devices.

Pharmaceutical delivery devices have been known for some time. They may be used as dressings, for example for transdermal delivery of pharmaceutically active materials or for implantation or insertion in a human or animal body, for example in cavities of the body or under the skin. One of the most acceptable materials used for making such devices is a silicone material and more particularly a silicone elastomeric material. These materials are usually employed to make a matrix in which the pharmaceutically active materials are loaded. The suitability of silicone elastomeric materials for use in pharmaceutical delivery devices is due in part to the relatively high permeability of such elastomers with respect to the pharmaceutically active components, when compared with other synthetic materials. It is also due to their excellent biocompatibility.

As silicone materials are hydrophobic in nature they are best suited for the delivery of non-polar or hydrophobic pharmaceutically active materials. In order to make the delivery of polar or hydrophilic pharmaceutically active materials from silicone based delivery devices possible, additives may be used or the nature of the silicone materials may be altered. For example in U.S. Pat. No. 3,832,458 a water permeable composition is provided which comprises a copolymer of a polysiloxane and N-vinyl pyrrolidone, wherein said N-vinyl pyrrolidone is in poly(N-vinyl pyrrolidone) chains grafted to a crosslinked polysiloxane elastomeric matrix, said copolymer having limited but significant permeability toward water soluble drugs. This composition forms the container wherein a water soluble drug is enclosed. Such containers have a distinct disadvantage in that a possible rupture of the container may have disastrous consequences, for example when a high concentration of the drug has toxic effects.

A different system has been proposed in U.S. Pat. No. 4,053,580 which discloses a microsealed pharmaceutical delivery device comprising a sectioned length of flexible medical grade silicone tubing as a biologically acceptable polymer container with as many perforations in the wall of the tubing when unsealed at each end as to expose up 40% of an inner biologically acceptable silicone polymer matrix contained within the biologically acceptable polymer container, said biologically acceptable polymer matrix having the formula

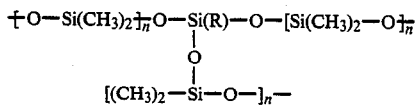

wherein R is alkoxy having 1 to 7 carbon atoms, alkyl having 1 to 10 carbon atoms, phenyl, vinyl or allyl, wherein n is about 100–5000 and having 10 to 200 micron microsealed compartments throughout, said microsealed compartments containing pharmaceutical saturated 20–70 w/v% polyethylene glycol molecular weight 450–6000, 20–70 v/v% propylene glycol or 20–70% 1-3-butanediol in water as hydrophilic solvent system.

There is a continuing search for improved pharmaceutical delivery devices, for example devices which can deliver a low level of a pharmaceutically active material over an extended period of time. An improved method for a more consistent and controllable manufacture of such delivery devices is also sought.

A device capable of a more prolonged delivery time requires a higher loading or concentration of a pharmaceutically active material. There is especially a need for such devices for the delivery of polar or hydrophilic pharmaceutically active materials.

We have now found that improved pharmaceutical delivery devices can be made from silicone elastomeric materials when certain surface active materials are used in their manufacture. These improved devices have the ability to accept an increased loading of polar or hydrophilic pharmaceutically active materials.

This invention accordingly provides a pharmaceutical delivery device comprising (A) a biologically acceptable silicone polymer matrix, (B) an organopolysiloxane-polyoxyalkylene copolymer, which is effective as a dispersing agent in the production of a water-in-oil emulsion in which the continuous phase comprises a silicone component, and (C) a drug component which is a polar or hydrphilic liquid comprising a pharmaceutically active material, said liquid being dispersed throughout the matrix (A) in small compartments having on average a diameter below 20 microns.

The biologically acceptable silicone polymer matrix (A), for use in the pharmaceutical delivery device of the invention, comprises a crosslinked silicone elastomeric material. Such silicone elastomeric materials may be produced from organosilicone compositions by crosslinking silicone polymers with or without the presence of crosslinking agents. Such crosslinking may be performed at elevated or at ambient temperatures. Preferred polymer matrix (A) materials are those obtained by curing the so-called room temperature vulcanising (RTV) organosilicone compositions. Such compositions do not require the application of high temperatures to effect cure. Their use thus reduces the risks of an adverse effect on the pharmaceutically active materials during the curing step. Examples of crosslinkable organosilicone compositions include organopolysiloxanes having silicon-bonded hydroxyl groups which may be crosslinked to elastomers by the addition of a crosslinking agent and a condensation catalyst. In such compositions the organopolysiloxane is generally a polydiorganosiloxane having terminal silanol groups. The crosslinking agent may be for example an alkoxy silane or an alkyl polysilicate e.g. methyltrimethoxysilane or ethyl polysilicate, or it may be an alkylhydrogen polysiloxane e.g. a polymethylhydrogensiloxane. A variety of catalysts may be employed, the organic metal compounds e.g. stannous octoate, dibutyltin dilaurate, alkyl titanates and titanium forming compositions are well known in the art and have been described in for example British Pat. Nos. 841 825, 844 128, 957 255 and 962 061. A more preferred elastomer-forming crosslinkable composition for producing polymer matrix (A) comprises an organopolysiloxane having per molecule at least two silicon-bonded groups having olefinic unsaturation, an organosilicon compound having at least two silicon-bonded hydrogen atoms and a catalyst, e.g. a platinum compound or complex which promotes the reaction between olefinic groups and silicon-bonded hydrogen atoms. Such compositions are particularly preferred because no by-products are produced during the crosslinking reaction. In addition little or no shrinkage occurs during crosslinking. This permits a more accurate manufacture of the devices with respect to their shape and size. Compositions of the preferred type are also well known in the art (see for example British Patent Specifications Nos. 1 090 122, 1 141 868 and 1 409 223) and commercially available. Typically such compositions comprise (a) a polydiorganosiloxane, which may vary from a freely flowing to a highly viscous liquid which comprises units of the general formula $$Q_a Q'SiO_{\frac{3-a}{2}} \text{ and } Q_b SiO_{\frac{4-b}{2}},$$

wherein Q denotes a monovalent hydrocarbon or substituted hydrocarbon group having no more than 8 carbon atoms, Q' denotes an organic group having olefinic unsaturation, e.g. vinyl, allyl or hexenyl, vinyl being generally preferred, at least 80% of the remaining silicon-bonded substituents being methyl, a has a value of 1 or 2 and b has a value of 0, 1, 2 or 3, (b) an organohydrogensiloxane having at least 2 silicon-bonded hydrogen atoms per molecule and wherein the remaining silicon-bonded substituents are monovalent hydrocarbon groups having no more than 8 carbon atoms, preferably being methyl groups, and (c) a Pt containing compound or complex, for example chloroplatinic acid, platinum acetylacetonate, complexes of platinous halides with unsaturated compounds such as ethylene, propylene, organovinylsiloxanes and styrene, hexamethyldiplatinum and Pt(CN)$_3$.

The organopolysiloxane-polyoxyalkylene copolymer (B) is a copolymer which is capable of functioning as a dispersing agent to facilitate the production of water-in-oil emulsions which have a silicone material in the continuous oil-phase. Examples of such copolymers are described for example in EP Specification No. 125 779 which provides an organopolysiloxane-polyoxyalkylene copolymer having the formula Z(Me)$_2$SiO[(Me)$_2$SiO]$_x$[(Me)(R)SiO]$_y$[(Me)(AR')SiO]$_z$Si(Me)$_2$Z wherein Me denotes a CH$_3$ radical, A denotes a polyoxyalkylene radical having the formula —(OCH$_2$CH$_2$)$_p$(OCHCH$_3$CH$_2$)$_q$OR", R denotes an alkyl radical having from 16 carbon atoms, R' denotes an alkylene radical linking A to the silicon atom, R" denotes a hydrogen atom or an alkyl radical having from 1 to 4 inclusive carbon atoms, Z denotes a monovalent hydrocarbon radical having from 1 to 16 carbon atoms or a AR' radical, there being an average of at least one AR' radical and at least one R radical per molecule and the average values of x, y, z, p and q being such that p>q, p+q has a value sufficient to provide a radical weight for A of from 600 to 3500, x<3y, x+y+z has a value of from 30 to 400 and the total weight of A radicals in the organopolysiloxane-polyoxyalkylene copolymer does not exceed a value of about ⅓ of the total weight of the organopolysiloxane. Other suitable copolymers (B) are described in G.B. Patent Specification No. 2 065 687 which provides an organopolysiloxane-polyoxyalkylene copolymer containing at least one polydiorganosiloxane segment comprising siloxane units of the formula $$R_b SiO_{\frac{4-b}{2}}$$

wherein b has a value of from 0 to 3 inclusive, there being an average of approximately 2 R radicals per silicon atom in the copolymer and R represents a methyl, ethyl, vinyl, phenyl or a divalent radical bonding a polyoxyalkylene segment to the polydiorganosiloxane segment, at least 95% of all R radicals being methyl and at least one polyoxyalkylene segment having an average molecular weight of at least 1000 and consisting of from 0 to 50 mol percent polyoxypropylene units and from 50 to 100 mol percent polyoxyethylene units, at least one terminal portion of the polyoxyalkylene segment not bonded to the polydiorganosiloxane segment being satisfied by a terminating radical, the weight ratio of polydiorganosiloxane segments to polyoxyalkylene segments in the copolymer having a value of from 2/1 to 8/1. The copolymers described in G.B. 2 065 687 are especially useful as they assist the formation of a stable water-in-oil emulsion without the need to heat or excessively shear the mixture of oil phase, water phase and emulsifier.

The drug component (C) is a polar or hydrophilic liquid comprising a pharmaceutically-active material. By the expression "polar or hydrophilic liquid" is meant a substance that is liquid at 25° C. under normal atmospheric pressure (760 mmHg) and which has a tendency to form or to migrate to the discontinuous phase of an emulsion wherein the continuous phase comprises mainly a polydiorganosiloxane compound and the emulsifying agent comprises an organopolysiloxane-polyoxyalkylene copolymer (B) as described above. The drug compound (C) may thus be a liquid polar or hydrophilic pharmaceutically active material per se, or a pharmaceutically active material which is dispersed or dissolved in a polar or hydrophilic solvent system. A polar or hydrophilic pharmaceutically active material for use in the delivery device of the invention may be any such material which is beneficially administered at a constant low dosage. They are usually water-soluble materials. Such pharmaceutically active materials include for example phenylephrine HCl, hydrocortisone, indomethacin, nisedipine, resorcinol, tetracyclin and pharmaceutically acceptable salts of many active materials, including free base types such as progesterone, propanolol and nicotine. If the pharmaceutically active material is itself liquid at 25° C. under atmospheric pressure, it may be used alone as the drug component (C). It may also be mixed with a polar or hydrophilic solvent system. Such solvent system allows the use of pharmaceutically active materials which are not liquid at 25° C. and normal atmospheric pressure. The solvent system may be a single solvent or it may consist of a mixture of several solvents. A particularly useful solvent system is water, glycol, amide, ethylene oxide adduct of alkyl phenols or a mixture of two or more of these. Other pharmaceutically acceptable water-miscible solvents may, however, be employed. Co-solvents such as for example polyethylene glycol, can be employed to improve the solubility of polar or hydrophilic pharmaceutically active materials in the solvent system. A particularly useful hydrophilic solvent system comprises polyethylene glycol, having a molecular weight of from about 200 to about 2000. By varying the polarity or hydrophilicity of the solvent system it may be adapted to give a greater affinity for pharmaceutically active materials with a varying degree of polarity and hydrophilicity. This will affect the rate and extent of release of the pharmaceutically active material from the delivery device. The presence of a polar or hydrophilic solvent in the drug component is believed to improve the delivery of pharmaceutically active materials from the device when in use. Since polar or hydrophilic pharmaceutically active materials have a greater affinity for hydrophilic solvents than for non-polar solvents, they will therefore preferably be located in the small compartments of (C) in the matrix (A). A smaller amount may, however, be found dispersed in the matrix (A) itself.

The pharmaceutical delivery device of the invention may also comprise other optional components. Such components may be added to alter the physical properties of the silicone matrix, to facilitate manufacture or to improve the usefulness of the delivery device.

The physical properties of the matrix are believed to influence the manner in which pharmaceutically active materials are released from the device of the invention. For example, it is believed that the more tightly cross-linked the silicone matrix the lower will be the rate of delivery of the pharmaceutically active material. Also, devices having a matrix of relatively high tensile strength are more suitable for use for implantation in the body, whilst physically weaker devices are more likely to be used for transdermal delivery. Components which may be employed to influence the physical properties of the pharmaceutical delivery device include for example unreactive silicone polymers e.g. those having the general formula $R_3Si[OSiR_2]_nR$, wherein R denotes an alkyl or aryl group having up to about 18 carbon atoms each, and n is an integer, and cyclic polysiloxanes of the general formula $[R_2SiO]_n$, wherein R and n are as defined above. Silicone polymers having a low viscosity, e.g. below 200 mm$^2$/s are especially useful for reducing the hardness of the matrix. According to another technique volatile additives such as the low molecular weight silicone polymers described above may be incorporated into the silicone elastomer-forming composition during fabrication of the matrix. The additive may thereafter be removed by volatilisation to provide a matrix having increased permeability with respect to the pharmaceutically-active material.

As the silicone matrix is itself hydrophobic in nature it is possible, and at times even advantageous, to include non-polar or hydrophobic pharmaceutically active materials in the device as this allows the simultaneous delivery of different types of pharmaceutically-active materials. The hydrophobic or non-polar materials may be incorporated in the silicone matrix according to methods known in the art. Examples of such hydrophobic or polar pharamaceutically active materials include for example nicotine, chlorophenylamine, propanolol and progesterone. The incorporation or such materials may be facilitated with the aid of a carrier e.g. a silicone polymer of low viscosity.

The pharmaceutical delivery device of the invention has dispersed throughout the silicone matrix (A) compartments of the drug component (C) having on average a diameter of less than 20 microns. These small compartments contain the polar or hydrophilic liquid which comprises a pharmaceutically active material. The preferred delivery device of the invention has compartments with an average diameter of less than 10 microns. Most preferably the diameter is less than 5 microns. The smaller the diameter of the compartments, the greater the possible content of the pharmaceutically active materials in the device. The optimum amount of pharmaceutically-active material to be incorporated in the delivery device will depend for example on the desired useful life of the device and rate of delivery of the active substance. It has been found that at least 10% by weight of active substance, based on the total weight of the device, can be incorporated without diminishing the performance of the delivery device.

The pharmaceutical delivery device of the invention may be produced by forming in the presence of the organopolysiloxane-polyoxyalkylene copolymer (B), a dispersion of the drug component (C), in the silicone elastomer-forming composition which is the precursor for matrix (A), and thereafter curing the elastomer-forming composition.

Such a process is believed to be novel and the invention accordingly provides in another of its aspects a process for preparing a pharmaceutical delivery device comprising the stages of (I) dispersing in the presence of an organopolysiloxane-polyoxyalkylene copolymer, which is effective as a dispersing agent in the production of an emulsion comprising water dispersed in a silicone or silicone-containing continuous phase, a drug component which is a polar or hydrophilic liquid comprising a pharmaceutically active material in an elastomer-forming organosilicone composition and (II) thereafter curing said elastomer-forming composition.

In a preferred process there is first prepared an emulsion of the polar or hydrophilic liquid comprising a pharmaceutically active material in an oil using the organopolysiloxane-polyoxyalkylene copolymer as emulsifier. The continuous (oil) phase of the emulsion preferably comprises a silicone oil. This silicone oil may be for example a low viscosity silicone organosiloxane polymer or a component or portion of the organosilicone elastomer-forming composition. The dispersion of the drug component throughout the matrix is improved by this process compared to a process where all components are mixed together in a single operation during stage (I).

In the preferred process of the invention, stage (I) comprises the steps of (1) making an emulsion by mixing together an organopolysiloxane-polyoxyalkylene copolymer, a polar or hydrophilic liquid comprising a pharmaceutically active material and an organosiloxane polymer, (Z) mixing the emulsion with an organosilicone composition which is elastomer-forming per se or upon the incorporation of the organosiloxane polymer employed in (1).

In step (1) of the preferred method of the invention standard emulsification techniques may be used. Using the organopolysiloxane-polyoxyalkylene copolymers (B) an emulsion can be obtained which is stable pending incorporation in the matrix and which, if desired, has an average particle size below 20 microns. The mixing of the components of the emulsion may be carried out in standard emulsification equipment. The amount of organopolysiloxane-polyoxyalkylene copolymer (B) which is employed in step (1) may conveniently be up to 5% by weight of the total weight of the emulsion. Preferably from 0.05 up to 1% by weight is used. The amount of the polar or hydrophilic liquid which may be used in step (1) of the process of the invention may vary according to the amount of the pharmaceutically-active material desired in the delivery device and, when a solvent is present, is according to the solubility or dispersibility of the pharmaceutically-active material in the solvent. Usually polar or hydrophilic liquid will make up from 5 to 50% of the total weight of the emulsion, although smaller and larger amounts are also possible.

The organosiloxane polymer employed in step (1) of the preferred method of the invention is conveniently a polydiorganosiloxane. Such polydiorganosiloxanes include linear triorganosiloxy end-blocked polydiorganosiloxanes such as e.g. trimethylsiloxy end-blocked polydimethylsiloxanes. They also include cyclic diorganopolysiloxanes of the general formula $[R_2SiO]_n$, wherein R represents a hydrocarbon radical having 1 to 16 carbon atoms. Most conveniently the organosiloxane polymer comprises cyclic diorganopolysiloxanes e.g. octamethylcyclotetrasiloxane or polydiorganosiloxanes having a viscosity of from about 0.65 mm²/s to about $1 \times 10^{-2}$ m²/s at 25° C. The presence of these materials appears to facilitate the formation of the desired emulsion. The low viscosity silicone material may be incorporated separately or together with other components of the emulsion, for example as a mixture with the organopolysiloxane-polyoxyalkylene copolymer (B). The amount of low viscosity silicone polymers which may be included in this step may constitute up to 95% by weight of the total weight of the water-in-oil emulsion, especially when the only organopolysiloxane polymer used are the low viscosity silicone polymers. Any hydrophobic pharmaceutically active materials which it may be desired to incorporate may be pre-dispersed or dissolved in the silicone material, for example in the low viscosity silicone polymer, prior to mixing this with the other components of the composition which is to be emulsified. If desired the organosiloxane polymer used in step (1) of the preferred process may comprise one or more of the silicone components of the elastomer-forming material. The emulsion may then be mixed in step (2) of the preferred process of the invention with the remainder of the elastomer-forming composition to enable curing to take place. For example in the case of the preferred (platinum curable) elastomer-forming compositions the organosiloxane polymer of step (1) may comprise a portion of the base polymer, that is the organopolysiloxane having per molecule at least two silicon-bonded olefinically unsaturated groups.

In step (2) of the preferred process for making delivery devices of this invention the emulsion and the components of the elastomer-forming composition may be mixed in any order. During the mixing step sufficient shear may be applied to cause the diameter of the small compartments which form the discontinuous phase of the emulsion to be further reduced. The weight ratio of emulsion, as prepared in step (1) to elastomer-forming material may vary depending on the proportion of pharmaceutically active material desired in the delivery device and on the required rate of delivery of the active material. Up to about 40% by weight of the emulsion based on the total weight of the device can be incorporated successfully without reducing the efficiency of the pharmaceutical delivery device. Hydrophobic pharmaceutically-active materials may also be introduced with the elastomer-forming composition introduced in step (2) of the preferred method of the invention.

During stage (II) of the process of the invention the elastomer-forming composition is then cured by any appropriate means. Depending on the type of elastomer-forming material employed curing may be effected at low or at normal ambient temperatures or by exposure to elevated temperatures and/or high energy radiation.

It is believed that the method of the invention provides an improvement over the methods of the prior art. A method for making biologically acceptable silicone polymer matrix adapted for placement in a tubing and having 10-200 micron microsealed compartments, containing a pharmaceutical in a hydrophilic solvent system distributed throughout, as disclosed in U.S. Pat. No. 3,992,518 comprises (a) emulsifying the hydrophilic solvent system of water and liquid polyethylene glycol containing the pharmaceutical saturated therein, and stannous octoate crosslinking agent, and biologically acceptable room temperature vulcanising liquid polydimethylsiloxane silicone polymer, and (b) in situ crosslinking the biologically acceptable liquid silicone polymer to form the biologically acceptable silicone polymer matrix with microsealed compartments throughout containing pharmaceutical and hydrophilic solvent system. Another method is described in EP No. 137 278 where there is provided a method for the production of a means for the transdermal application of pharmaceutically active materials, wherein at least 50% of the pharmaceutically active material is dissolved in a non-volatile physiologically harmless gel, which is suspended in the components required to make a crosslinked silicone elastomer, and in that the suspension is then crosslinked.

The emulsification process described in U.S. Pat. No. 3,992,518 is obtained by dispersing a saturated solution of pharmaceutical in water and hydrophilic solvent throughout liquid silicone polymer by means of high speed stirring before crosslinking the polymer. However, this does not permit close control of the size or the distribution of the microsealed compartments in the polymer matrix. Whilst the polymer matrix is being shaped ad crosslinked the compartments formed during the high speed stirring will tend to coalesce and hence form larger compartments. Such coalescence will reduce the load capacity of the matrix and affect deleteriously its drug release characteristics. The method described in EP Specification No. 137 278 requires a very high shear to break up the gel particles in the silicone matrix. This also makes it more difficult to control accurately the size of the dispersed gel particles and hence it affects the release properties of the pharmaceutically active materials from the delivery device.

The method of the present invention produces a delivery device in which the diameter of the small compartments can be accurately controlled. It has been found possible to achieve a compartment diameter of less than 20 microns for a large proportion of the compartments present. Due to the stability of the formed dispersion the tendency to coalesce is also greatly reduced. Using the preferred method of the invention wherein an emulsion is formed and using a low viscosity silicone material as the organosiloxane polymer compartments having on average a further reduced diameter may be obtained during the mixing step (2). In some cases on average a diameter of less than 5 microns can be consistently achieved. Moreover the use of a preferred hydrophilic solvent system which comprises polyethylene glycol in the polar or hydrophilic liquid makes it possible to achieve consistently on average a compartment diameter below 5 microns.

There now follow examples in which parts are expressed by weight, unless otherwise stated, which illustrate the invention. In these examples Me denotes a methyl group and Vi a vinyl group.

EXAMPLE 1

Illustrative Process (a) Making the Emulsion

A first solution was made by stirring together for 15 minutes 23.6 g of an organosiloxane polymer consisting of low viscosity volatile silicone materials (about 80% octamethylcyclotetrasiloxane and 20% decamethylcyclopentasiloxane) and 0.4 g of an organopolysiloxane-polyoxyalkylene copolymer. The copolymer was prepared from a trimethylsiloxane-endblocked polydimethylsiloxane having a molecular weight of approximately 30,000, and having an average of approximately 4 of its dimethylsiloxane units replaced with methylhydrogensiloxane units, and a random equimolar polyglycol copolymer of ethylene oxide and propylene oxide having an average molecular weight of approximately 2550, and having allyloxy endgroups on one end and acetoxy endgroups on the other end. Prepartion of the copolymer was carried out by mixing 220 g of the siloxane, 80.76 g of the polyglycol, 75.19 g of isopropanol and 0.15 ml of a 1 molar solution of chloroplatinic acid in isopropanol as catalyst. The reaction mixture was heated under nitrogen at reflux for one hour and then devolatilized at 110° C. and 1.33 kPa pressure to yield a polydimethylsiloxane-polyoxyalkylene copolymer having a siloxane/oxyalkylene weight ratio of approximately 2.7 and —CH$_2$CH$_2$CH$_2$O— divalent radicals bonding the polyoxyalkylene portion to the polydimethylsiloxane portion by way of a silicon-carbon bond.

A second solution of 22 g of polyethylene glycol (PEG) in 20 g of distilled water was made thus forming a liquid hydrophilic medium which was dropwise added to the first solution under stirring. A stable water-in-oil emulsion was obtained.

(b) Making the Delivery Device

To 200 g of an organopolysiloxane composition having a viscosity of about $1.5 \times 10^5$ mm$^2$/s and comprising 100 parts of polydiorganosiloxane having vinyl groups bonded to silicon atoms, 35 parts of a silica filler and a Pt containing catalyst, the water-in-oil emulsion was added dropwise under stirring on a high shear mixer resulting in a first dispersion. Then 20g of a mixture of about 90 parts of a vinyl containing polydiorganosiloxane and 10 parts of a methylhydrogensiloxane material, which together with the organopolysiloxane composition forms an elastomer-forming composition, was stirred into the first dispersion. The second dispersion thus formed was then subjected to reduced pressure to degas during 10 minutes, cast in moulds and allowed to cure for 40 minutes at 60° C. in order to allow the elastomer-forming composition to form a matrix resulting in a base delivery device without any pharmaceutically-active material.

Illustrative Delivery Devices

Devices prepared employing the above described method were found to have at the emulsion stage compartments with an average diameter of 10.5 microns when the polyethylene glycol was omitted. When the polyethylene glycol used had an average molecular weight of 400 the average diameter dropped to 5 microns, with 100% of the compartments having a diameter of 17.7 microns or below. When the polyethylene glycol used had a molecular weight of 600 the diameter was 3.9 microns on average, with all compartments having a diameter of 13.6 microns or below. After mixing the latter water-in-oil emulsion with the elastomer-forming composition the diameter was further reduced to an average of 3 microns, with 100% of the compartments having a diameter of 10.5 microns or below. These sizes were retained when the device was cured.

EXAMPLES 2 TO 10

Using the process described in Example 1 nine water-in-oil emulsions were prepared, each containing a pharmaceutically-active substance. The substances employed were progesterone (Drug A), propanolol HCl (Drug B) and indomethacin (Drug C). Each substance was incorporated by addition to the second solution described in Example 1 in quantities of 23.43 g, 14.26 g or 7.29 g.

| Emulsion | PEG 400 | Water | Drug (Type/Quantity) |
|---|---|---|---|
| A1 | 22 | 20 | A/23.43 |
| A2 | 22 | 20 | A/14.26 |
| A3 | 22 | 20 | A/7.29 |
| B1 | 22 | 20 | B/23.43 |
| B2 | 22 | 20 | B/14.26 |
| B3 | 22 | 20 | B/7.29 |
| C1 | 22 | 20 | C/23.43 |
| C2 | 22 | 20 | C/14.26 |
| C3 | 22 | 20 | C/7.29 | wherein PEG 400 stands for polyethylene glycol having a molecular weight of 400 and wherein the quantity of the drug used is expressed in grams.

Pharmaceutical delivery devices (A' 1—3, B' 1—3 and C' 1—3) according to the invention were prepared by mixing sufficient of the respective water-in-oil emulsions with the elastomer-forming composition as descrined in Example 1 to obtain a 5% by weight loading of the drugs in the delivery device, that is respectively 10, 20 and 40% of the emulsion, based on the total weight of the device. The mixtures were then further processed as in Example 1.

Comparative pharmaceutical release devices (A'*, B'* and C'*) were prepared by mixing Drug A, B and C respectively per se with the elastomer-forming composition as described in Example 1, in ratios so as to give 5% by weight of the drug in the device.

The moulded and cured pharmaceutical delivery devices thus prepared were die cut into 20 mm diameter discs and were placed in the stainless steel basket assembly in a Vanderkamp Model 600 USP Dissolution System (Van Kel Industries, Edison, N.J., U.S.A.). Dissolution was evaluated in a solvent of 40% polyethylene glycol 400 at 37° C. at 425 rpm over a period of 24 hours. Drug release characteristics of the devices were measued using U.V. spectrophotometry.

It was found that in all cases the drug release rate of the devices according to the invention was 2 to 5 times higher than for the comparative devices, the rate increasing with increased loading of water-in-oil emulsion in the devices.

EXAMPLES 11 TO 19

Similar emulsions were prepared as in Examples 2 to 10, except that the water in the liquid phase was replaced with nonoxynol-9 (an ethoxylated nonyl phenol). Pharmaceutical delivery devices made with these emulsions showed similarly improved properties as those of Examples 11 to 19.

That which is claimed is:

1. A pharmaceutical delivery device comprising (A) a biologically acceptable silicone polymer matrix, (B) an organopolysiloxane-polyoxyalkylene copolymer, which is effective as a dispersing agent in the production of a water-in-oil emulsion in which the continuous phase comprises a silicone component and (C) a drug component which is selected from polar and hydrophilic liquids comprising a pharmaceutically-active material, said liquid being dispersed throughout the matrix (A) in small compartments having on average a diameter below 20 microns.

2. A pharmaceutical delivery device according to claim 1 wherein the small compartments of (C) have on average a diameter below 10 microns.

3. A pharmaceutical delivery device according to claim 2 wherein the small compartments of (C) have on average a diameter below 5 microns.

4. A pharmaceutical delivery device according to Claim 1 wherein the organopolysiloxane-polyoxyalkylene copolymer (B) has the average formula

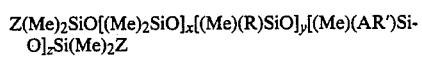

wherein Me denotes a $CH_3R$ radical, A denotes a polyoxyalkylene radical having the formula $-(OCH_2CH_2)_p(OCHCH_3CH_2)_qOR''$, R denotes an alkyl radical having from 6 to 16 carbon atoms, R' denotes an aklylene radical linking A to the silicon atom, R" is selected from the group consisting of a hydrogen atom and an alkyl radical having from 1 to 4 inclusive carbon atoms, Z is selected from the group consisting of a monovalent hydrocarbon radical having from 1 to 16 carbon atoms and a AR' radical, there being an average of at least one AR' radical and at least one R radical per molecule and the average values of x, y, z, p and q being such that p>q, p+q has a value sufficient to provide a radical weight for A of from 600 to 3500, x<3y, x+y+z has a value of from 30 to 400 and the total weight of A radicals in the organo- polysiloxane-polyoxyalkylene copolymer does not exceed a value of about ⅓ of the total weight of the organopolysiloxane.

5. A pharmaceutical delivery device according to claim 1 wherein the organopolysiloxane-polyoxyalkylene copolymer (B) contains at least one polydiorganosiloxane segment comprising siloxane units of the formula

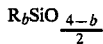

wherein b has a value of from 0 to 3 inclusive, there being an average of approximately 2 R radicals per silicon atom in the copolymer and R is selected from the group consisting of methyl, ethyl, vinyl, phenyl and a divalent radical bonding a polyoxyalkylene segment to the polydiorganosiloxane segment, at least 95% of all R radicals being methyl and at least one polyoxyalkylene segment having an average molecular weight of at least 1000 and consisting of from 0 to 50 mol percent polyoxypropylene units and from 50 to 100 mol percent polyoxyalkylene units, at least one terminal portion of the polyoxyalkylene segment not bonded to the polydiorganosiloxane segment being satisfied by a terminating radical, the weight ratio of polydiorganosiloxane segment to polyoxyalkylene segments in the copolymer having a value of from 2/1 to 8/1.

6. A pharmaceutical delivery device according to claim 1 wherein the biologically acceptable silicone polymer matrix (A) results from the curing of a room temperature vulcanising organosilicone composition.

7. A pharmaceutical delivery device according to claim 1 wherein the biologically acceptable silicone polymer matrix (A) results from the curing of an elastomer-forming composition which comprises an organopolysiloxane having per molecule at least 2 silicon-bonded groups having olefinic unsaturation, an organosilicon compound having at least 2 silicon-bonded hydrogen atoms and a catalyst which promotes the reaction between olefinic groups and silicon-hydrogen groups.

8. A pharmaceutical delivery device according to claim 1 wherein the drug component (C) is selected from polar and hydrophilic liquid pharmaceutically active materials.

9. A pharmaceutical delivery device according to claim 1 wherein the drug component (C) is a pharmaceutically active material dispersed in one or more solvents selected from polar and hydrophilic solvents.

10. A pharmaceutical delivery device according to claim 1 wherein the drug component (C) is a pharmaceutically active material dissolved in one or more solvents selected from polar and hydrophilic solvents.

11. A pharmaceutical delivery device according to claim 9 wherein the solvent comprises polyethylene glycol having a molecular weight of from 200 to 2000.

12. A pharmaceutical delivery device according to claim 10 wherein the solvent comprises polyethylene glycol having a molecular weight of from 100 to 2000.

13. A pharmaceutical delivery device according to claim 1 wherein the device also comprises silicone polymers having a viscosity below 200 $mm^2/s$.

14. A pharmaceutical delivery device according to claim 1 wherein the device also comprises a non-polar or hydrophobic pharmaceutically active material.

15. A process for making a pharmaceutical delivery device comprising stage (I) dispersing a drug component which is selected from polar and hydrophilic liquids comprising a pharmaceutically active material in an elastomer-forming organosilicone composition in the presence of an organopolysioxane-polyoxyalkylene copolymer, which is effective as a dispersing agent in the production of an emulsion comprising water dispersed in a silicone-containing continuous phase and stage (II) thereafter curing said elastomer-forming composition.

16. A process according to claim 15 wherein stage (I) comprises the steps of (1) preparing an emulsion by mixing together the organopolysiloxane-polyoxyalkylene copolymer, the polar or hydrophilic liquid medium comprising a pharmaceutically active material and an organosiloxane polymer, and (2) mixing the emulsion with an organosilicone composition which is elastomer-forming.

17. A process according to claim 15 wherein stage (I) comprises the steps of (1) preparing an emulsion by mixing together the organopolysiloxane-polyoxyalkylene copolymer, the polar or hydrophilic liquid medium comprising a pharmaceutically active material and an organosiloxane polymer, and (2) mixing the emulsion with an organosilicone composition which is elastomer-forming upon the incorporation of the organosiloxane polymer employed in step (1).

* * * * *